(12) United States Patent
Kunita

(10) Patent No.: US 6,787,622 B2
(45) Date of Patent: Sep. 7, 2004

(54) RADICAL POLYMERIZABLE COMPOUND HAVING AT LEAST ONE CONNECTING HETERO ATOM

(75) Inventor: Kazuto Kunita, Shizuoka (JP)

(73) Assignee: Fuji Photo Film Co., Ltd., Minami-Ashigara (JP)

( * ) Notice: Subject to any disclaimer, the term of this patent is extended or adjusted under 35 U.S.C. 154(b) by 142 days.

(21) Appl. No.: 10/096,879

(22) Filed: Mar. 14, 2002

(65) Prior Publication Data

US 2003/0008996 A1 Jan. 9, 2003

(30) Foreign Application Priority Data

Mar. 14, 2001 (JP) .................................. P2001-072433

(51) Int. Cl.[7] .............................................. C08F 28/06
(52) U.S. Cl. ...................... 526/257; 526/259; 526/266; 526/287; 526/288; 526/298; 526/305; 526/333
(58) Field of Search ................................ 526/257, 259, 526/266, 298, 305, 287, 288, 333

(56) References Cited

U.S. PATENT DOCUMENTS

| | | | |
|---|---|---|---|
| 3,228,954 A | | 1/1966 | Durham et al. |
| 3,318,939 A | | 5/1967 | Durham et al. |
| 6,051,367 A | * | 4/2000 | Kunita et al. ............. 430/281.1 |
| 6,476,092 B1 | * | 11/2002 | Kunita ......................... 522/31 |

FOREIGN PATENT DOCUMENTS

| | | |
|---|---|---|
| DE | 1 966 828 A | 7/1974 |
| EP | 0 909 761 A1 | 4/1999 |
| EP | 1 091 247 A2 | 4/2001 |

OTHER PUBLICATIONS

Hoyle et al., Photopolymerization of a Semifluorinated Difunctional Liquid Crystalline Monomer in a Smectic Phase, Macromolecules, Apr. 22, 1996, pp 3182–3187, vol. 29, No. 9, American Chemical Society, Easton US, XP–000581771.
Jariwala et al., Syntheses, Polymerization, and Characterization of Novel Semifluorinated Methacrylates, Including Novel Liquid Crystalline Materials, Macromolecules, 1993, pp 5129–5136, vol. 26, American Chemical Society, Easton, US, XP–002071757.
Utsumi et al., Synthesis of Polymeric Anthraquinone Dyes, Kogyo Kagaku Zasshi, 1970, pp 1151–5, vol. 73, No. 6, Chemical Abstracts Database Accession No. 73:110849, XP–002260104.
Dybas et al., 2–(Substituted Piperidinomethyl)propenenitriles and Analogs as Preservatives for Aqueous Systems, Developments in Industrial Microbiology Series, vol. Date 1977, 1978, pp 347–53, vol. 19, Chemical Abstracts Database Accession No. 91:205628, XP–002260105.
Avci et al., Poly(.alpha.–hydroxymethylacrylates): esterification and crosslinking reactions, 1992, pp 239–44, vol. 3, Chemical Abstracts Database Accession No. 120:135232, XP–002260106.
Tanaka et al., Reactions of Bifunctional Addition–Fragmentation Chain Transfer Agents for Synthesis of Polymer Bearing Unsaturated Moieties at Both Ends, Macromolecular Chemistry and Physics, 2000, pp 1565–73, vol. 201, No. 14, Chemical Abstracts Database Accession No. 134:17795, XP–002260107.
Vo–Thanh et al., Ring–Closing Metathesis of Unsaturated Amides as a Route to Short and Medium–Sized Unsaturated Lactams and to Ethylenic Pseudopeptides, 2001, Synlett, pp 37–40, No. 1, Database Crossfire Beilstein Accession No. 134:280695, XP–002260108.
Wariishi, Crosslinked Polymers, Solid Polymer Electrolytes from Them, and Manufacture of the Electrolytes, JP 2000–017076 A, Jan. 18, 2000, Abstract, Chemical Abstracts Database Accession No. 132:93816, XP–002260109.
Database Crossfire Beilstein 'Online', Beilstein Institut zur Forderung der Chemischen Wissenschaften, Frankfurt am Main, Germany; Database accession No. Reaction ID 874924 XP002250649.
Database Crossfire Beilstein 'Online', Beilstein Institut zur Forderung der Chemischen Wissenschaften, Frankfurt am Main, Germany; Database accession No. BRN 3946206 XP002250650.
Database Crossfire Beilstein 'Online', Beilstein Institut zur Forderung der Chemischen Wissenschaften, Frankfurt am Main, Germany; Database accession No. Reaction ID 1504995 XP002250651.

(List continued on next page.)

Primary Examiner—Helen L. Pezzuto
(74) Attorney, Agent, or Firm—Burns, Doane, Swecker & Mathis, L.L.P.

(57) ABSTRACT

A radical polymerizable compound comprising a structure represented by the following formula (I), (II) or (III):

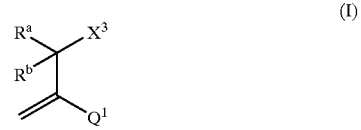

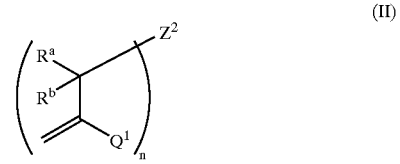

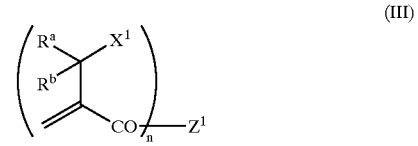

wherein the various groups and "n" in the formulas are defined and certain of the defined groups contain a hetero atom and are connected through the hetero atom.

7 Claims, No Drawings

OTHER PUBLICATIONS

Database Crossfire Beilstein 'Online', Beilstein Institut zur Forderung der Chemischen Wissenschaften, Frankfurt am Main, Germany; Database accession No. Reaction ID 1654505 XP002250652.

Database Crossfire Beilstein 'Online', Beilstein Institut zur Forderung der Chemischen Wissenschaften, Frankfurt am Main, Germany; Database accession No. Reaction ID 2582074 XP002250653.

Database Crossfire Beilstein 'Online', Beilstein Institut zur Forderung der Chemischen Wissenschften, Frankfurt am Main, Germany; Database accession No. BRN 5945911, 5934552 XP002250654.

Duygu Avic et al., "Photopolymerization Studies of Alkyl and Aryl Ester Derivatives of Ethyl α–Hydroxymethylacrylate", *Journal of Polymer Science: Part A: Polymer Chemistry*, vol. 34. No. 15. pp 3191–3201, 1996, John Wiley & Sons, Inc.

* cited by examiner

RADICAL POLYMERIZABLE COMPOUND HAVING AT LEAST ONE CONNECTING HETERO ATOM

FIELD OF THE INVENTION

The present invention relates to a novel radical polymerizable compound, more specifically to a radical polymerizable compound capable of utilizing for image forming materials, for example, stereolithography, holography, lithographic printing plate precursors, color proofs, photoresists and color filters, and photosetting resin materials, for example, ink, paint and adhesives. In particular, it relates to a radical polymerizable compound for use in a photopolymerizable composition suitable for the preparation of a lithographic printing plate precursor that is capable of being subjected to a so-called direct plate-making, in which the plate-making is directly conducted based on digital signals, for example, from a computer using various kinds of lasers.

BACKGROUND OF THE INVENTION

A solid laser, semiconductor laser and gas laser having a large output and a small size, which radiate an ultraviolet ray, visible light or infrared ray having a wavelength of from 300 to 1,200 nm, have become easily available, and these lasers are very useful for a recording light source used in the direct plate-making based on digital signals, for example, from a computer.

Various investigations on recording materials sensitive to such laser beams have been made. Typical examples thereof include recording materials capable of being recorded with a infrared laser having a wavelength of not less than 760 nm, for example, positive-working recording materials as described in U.S. Pat. No. 4,708,925 and acid catalyst crosslinking type negative-working recording materials described in JP-A-8-276558 (the term "JP-A" as used herein means an "unexamined published Japanese patent application"), and recording materials responsive to an ultraviolet ray or visible light laser having a wavelength of from 300 to 700 nm, for example, radical polymerization type negative-working recording materials as described in U.S. Pat. No. 2,850,445 and JP-B-44-20189 (the term "JP-B" as used herein means an "examined Japanese patent publication").

On the other hand, recording materials responsive to short wavelength light of not more than 300 nm are especially important for photoresist materials. In recent years, in integrated circuits, the degree of integration is more and more increased and in the production of a semiconductor substrate of VLSI, etc., fabrication of super-fine patterns composed of line width of finer than half micron has been required. In order to fulfill such requirements, the wavelength of light source used in an exposure apparatus in photolithography is more and more shortened and the use of a far ultraviolet ray or an excimer laser (e.g., XeCl, KrF or ArF) has been investigated. Further, the formation of super-fine patterns by an electron beam has been started to investigate. Particularly, the electron beam is regarded as a promising light source for pattern forming technique to lead the next generation.

A subject common to all of these image recording materials is that how an ON-OFF of the images can be enlarged. In other words, how high sensitivity and preservation stability of the image recording material can be stood together. Photo radical polymerization systems are ordinarily highly sensitive but their sensitivities severely decrease on polymerization inhibition due to oxygen in the air. Thus, measures of providing a layer for interrupting oxygen on an image forming layer are taken. However, the formation of such a layer for interrupting oxygen may cause fog due to polymerization in the dark, resulting in degradation of preservation stability. It is difficult for the high sensitivity to consist with the preservation stability and satisfactory results have not been obtained in the prior art. Therefore, novel techniques to solve these problems have been desired.

SUMMARY OF THE INVENTION

Therefore, an object of the present invention is to provide a radical polymerizable compound for use in a photo-radical polymerization composition satisfying both high sensitivity and excellent preservation stability, which is promising in image forming techniques due to the highest sensitivity.

Another object of the present invention is to provide a radical polymerizable compound for use in a photopolymerizable composition suitable for a lithographic printing plate precursor capable of performing direct plate-making based on digital data, for example, from a computer by recording using a solid laser or semiconductor laser radiating an ultraviolet ray, visible light or infrared ray.

Other objects of the present invention will become apparent from the following description.

As a result of the earnest investigations, it has been found that the above-described objects of the invention can be achieved by using a compound having a specific polymerizable group in a photopolymerizable composition.

Specifically, the radical polymerizable compound of the present invention has a structure represented by the following formula (I), (II) or (III):

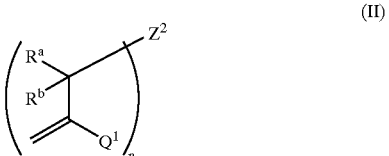

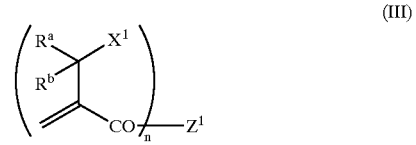

wherein $X^3$ represents a heterocyclic group that is connected through a hetero atom included therein; $Q^1$ represents a group represented by CN or $COX^2$; $X^2$ represents a hydroxy group, a substituted oxy group, a substituted thio group, an amino group, a substituted amino group, a heterocyclic group that is connected through a hetero atom included therein or a halogen atom; $X^1$ represents a substituted oxy group, a substituted amino group, a heterocyclic group that is connected through a hetero atom included therein or a halogen atom; $Z^1$ and $Z^2$ each represents a n-valent connecting group having at least 6 carbon atoms, in which the n's connecting parts are all hetero atoms; $R^a$ and $R^b$, which may be the same or different, each represents a hydrogen atom, a halogen atom, a cyano group or an organic residue; or $R^a$ and $R^b$, $X^1$ and $R^a$ or $R^b$ $X^3$ and $R^a$ or $R^b$, or $Q^1$ and $R^a$ or $R^b$ may combine with each other to form a cyclic structure; and n represents an integer of from 2 to 6.

DETAILED DESCRIPTION OF THE INVENTION

Monomers, oligomers and polymers containing a group having a high polymerization activity, for example, an acrylic ester group, an acrylamido group, a methacrylic ester group or a methacrylamido group have hitherto been employed as most common radical polymerizable compounds. However, since these compounds suffer the polymerization inhibition due to oxygen, when they are used in photopolymerizable compositions, the subject of securing both sensitivity and preservation stability cannot be achieved.

On the other hand, compounds (monomers) having an α-hetero-substituted methylacryl group or an α-halogen-substituted methylacryl group as a group having polymerizability comparing favorably with the acrylic groups are known for polymer constituting components. It is said that the polymerizability of such a compound for polymer constituting component increases owing to the electronic effect and steric effect of hetero atom or halogen atom substituted in the α-position different from groups having low polymerizability, for example, an itaconic acid group having a substituent in the α-position or an α-alkylacryl group.

It has been found that the difficulty which resides in conventional radical polymerizable compounds, specifically the effect of polymerization inhibition due to oxygen can be remarkably reduced by using a compound having a structure including a polymerizable group substituted with a hetero atom or a halogen atom in its α-position together with a photopolymerization initiator in a photopolymerizable composition, and that the subject of securing both high sensitivity and excellent preservation stability, which is an inherent problem in the photopolymerizable composition, can be achieved.

Although the mechanism of reducing the influence of polymerization inhibition due to oxygen is not certain, it is believed that the compound containing a structure represented by formula (I), (II) or (III) according to the present invention has an extremely small termination rate constant due to the effect of substituent on its α-position, while possessing a not particularly high polymer growth rate constant in comparison with conventional acrylic or methacrylic compounds, so that it hardly reacts with oxygen at the time of chain propagation, and as a result, it is scarcely influenced by the polymerization inhibition due to oxygen.

The compound having a structure represented by formula (I), (II) or (III) according to the present invention is described in detail below.

The compound including at least one polymerizable group according to the present invention has the structure represented by formula (I), (II) or (III).

The structure represented by formula (I), (II) or (III) may form a monovalent or two or more valent substituent, or a compound in which all of $R^a$, $R^b$, $X^1$, $X^2$ and $X^3$ in formula (I), (II) or (III) each represents a terminal group. When the structure represented by formula (I), (II) or (III) forms a monovalent or two or more valent substituent, at least one of $R^a$, $R^b$, $X^1$, $X^2$ and $X^3$ in formula (I), (II) or (III) has one or more bonds. Further, $X^1$, $X^2$ or $X^3$ in formula (I), (II) or (III) may form a connecting group having m's connectable parts, to terminals of which m's groups represented by formula (I), (II) or (III) are bonded (wherein m represents an integer of 2 or more) (multifunctional compound).

Moreover, the structure represented by formula (I), (II) or (III) may be bonded to a polymer chain at $X^1$, $X^2$ or $X^3$. In such a case, the structures represented by formula (I), (II) or (III) are present in side chains of the polymer chain. The polymer chain includes a linear organic polymer described hereinafter. Specific examples of the polymer include a vinyl polymer, e.g., polyurethane, novolak or polyvinyl alcohol, polyhydroxystyrene, polystyrene, poly(meth)acrylic ester, poly(meth)acrylamide and polyacetal. The polymer may be a homopolymer or copolymer.

In formula (I), (II) or (III), a hetero atom included in the heterocyclic group represented by $X^1$, $X^2$ or $X^3$ is preferably a non-metallic atom, and specifically includes an oxygen atom, a sulfur atom, a nitrogen atom and a phosphorus atom. The halogen atom represented by $X^1$ or $X^2$ include, for example, a chlorine atom, a bromine atom, an iodine atom and a fluorine atom.

$X^1$ represents a substituted oxy group, a substituted thio group, a heterocyclic group that is connected through a hetero atom included therein or a halogen atom.

$X^2$ represents a hydroxy group, a substituted oxy group, a substituted thio group, an amino group, a substituted amino group, a heterocyclic group that is connected through a hetero atom included therein or a halogen atom.

$X^3$ represents a heterocyclic group that is connected through a hetero atom included therein.

In the case wherein $X^1$, $X^2$ or $X^3$ represents a connecting group to which another substituent is bonded, m's groups represented by formula (I), (II) or (III) are bonded to terminals of a connecting group having m's connectable parts obtained by eliminating m's hydrogen atoms (wherein m represents an integer of 2 or more).

$R^a$ and $R^b$, which may be the same or different, each represents preferably a hydrogen atom, a halogen atom, a cyano group or as the organic residue, a hydrocarbon group which may have a substituent and/or an unsaturated bond, a substituted oxy group, a substituted thio group, a substituted amino group, a substituted carbonyl group or a carboxylato group. Alternatively, $R^a$ and $R^b$, $X^1$ and $R^a$ or $R^b$, $X^3$ and $R^a$ or $R^b$, or $Q^1$ and $R^a$ or $R^b$ may combine with each other to form a cyclic structure.

$Z^1$ and $Z^2$ each represents a n-valent connecting group having at least 6 carbon atoms, preferably at least 7 carbon atoms, in which the n's connecting parts are all hetero atoms. n represents an integer of from 2 to 6, and preferably an integer of from 3 to 6.

The hetero atoms at the n's connecting parts of $Z^1$ and $Z^2$ are selected from an oxygen atom, a sulfur atom, a nitrogen atom and a phosphorus atom, and preferably forms a substituted oxy group, a substituted thio group, an amino group, a substituted amino group or a heterocyclic group that is connected through a hetero atom included therein. The n's connecting parts of $Z^2$ contain more preferably a connecting structure of —OCO—.

The most preferred specific examples of $Z^1$ and $Z^2$ include connecting structures shown in specific examples of the compounds having a structure represented by formula (I), (II) or (III) set forth hereinafter.

Each of the substituents in $X^1$, $X^2$, $X^3$, $R^a$ and $R^b$ in formula (I), (II) or (III) is described below.

The hydrocarbon group which may have a substituent and/or an unsaturated bond includes an alkyl group, a substituted alkyl group, an aryl group, a substituted aryl group, an alkenyl group, a substituted alkenyl group an alkynyl group and a substituted alkynyl group.

The alkyl group includes a straight chain, branched or cyclic alkyl group having from 1 to 20 carbon atoms. Specific examples thereof include methyl, ethyl, propyl, butyl, pentyl, hexyl, heptyl, octyl, nonyl, decyl, undecyl, dodecyl, tridecyl, hexadecyl, octadecyl, eicosyl, isopropyl, isobutyl, sec-butyl, tert-butyl, isopentyl, neopentyl, 1-methylbutyl, isohexyl, 2-ethylhexyl, 2-methylhexyl, cyclohexyl, cyclopentyl and 2-norbornyl groups. Of the alkyl groups, a straight chain alkyl group having from 1 to 12 carbon atoms, a branched alkyl group having from 3 to 12 carbon atoms and a cyclic alkyl group having from 5 to 10 carbon atoms are preferred.

The substituted alkyl group is composed of a substituent bonding to an alkylene group. The substituent includes a monovalent non-metallic atomic group exclusive of a hydrogen atom. Preferred examples of the substituent for the alkyl group include a halogen atom (e.g., fluorine, bromine, chlorine or iodine), a hydroxy group, an alkoxy group, an aryloxy group, a mercapto group, an alkylthio group, an arylthio group, an alkyldithio group, an aryldithio group, an amino group, an N-alkylamino group, an N,N-dialkylamino group, an N-arylamino group, an N,N-diarylamino group, an N-alkyl-N-arylamino group, an acyloxy group, a carbamoyloxy group, an N-alkylcarbamoyloxy group, an N-arylcarbamoyloxy group, an N,N-dialkylcarbamoyloxy group, an N,N-diarylcarbamoyloxy group, an N-alkyl-N-arylcarbamoyloxy group, an alkylsulfoxy group, an arylsulfoxy group, an acylthio group, an acylamino group, an N-alkylacylamino group, an N-arylacylamino group, a ureido group, an N'-alkylureido group, an N',N'-dialkylureido group, N'-arylureido group, an N',N'-diarylureido group, an N'-alkyl-N'-arylureido group, an N-alkylureido group, N-arylureido group, an N'-alkyl-N-alkylureido group, an N'-alkyl-N-arylureido group, an N',N'-dialkyl-N-alkylureido group, an N',N'-dialkyl-N-arylureido group, an N'-aryl-N-alkylureido group, an N'-aryl-N-arylureido group, an N',N'-diaryl-N-alkylureido group, an N',N'-diaryl-N-arylureido group, an N'-alkyl-N'-aryl-N-alkylureido group, an N'-alkyl-N'-aryl-N-arylureido group, an alkoxycarbonylamino group, an aryloxycarbonylamino group, an N-alkyl-N-alkoxycarbonylamino group, an N-alkyl-N-aryloxycarbonylamino group, an N-aryl-N-alkoxycarbonylamino group, an N-aryl-N-aryloxycarbonylamino group, an acyl group, a carboxy group and a conjugate base group thereof (hereinafter, referred to as a carboxylato group), an alkoxycarbonyl group, an aryloxycarbonyl group, a carbamoyl group, an N-alkylcarbamoyl group, an N,N-dialkylcarbamoyl group, an N-arylcarbamoyl group, an N,N-diarylcarbamoyl group, an N-alkyl-N-arylcarbamoyl group, an alkylsulfinyl group, an arylsulfinyl group, an alkylsulfonyl group, an arylsulfonyl group, a sulfo group (—SO$_3$H) and a conjugate base group thereof (hereinafter, referred to as a sulfonato group), an alkoxysulfonyl group, an aryloxysulfonyl group, a sulfinamoyl group, an N-alkylsulfinamoyl group, an N,N-dialkylsulfinamoyl group, an N-arylsulfinamoyl group, an N,N-diarylsulfinamoyl group, an N-alkyl-N-arylsulfinamoyl group, a sulfamoyl group, an N-alkylsulfamoyl group, an N,N-dialkylsulfamoyl group, an N-arylsulfamoyl group, an N,N-diarylsulfamoyl group, an N-alkyl-N-arylsulfamoyl group, an N-acylsulfamoyl group and a conjugate base group thereof, an N-alkylsulfonylsulfamoyl group (—SO$_2$NHSO$_2$(alkyl)) and a conjugate base group thereof, an N-arylsulfonylsulfamoyl group (—SO$_2$NHSO$_2$(aryl)) and a conjugate base group thereof, an N-alkylsulfonylcarbamoyl group (—CONHSO$_2$(alkyl)) and a conjugate base group thereof, an N-arylsulfonylcarbamoyl group (—CONHSO$_2$(aryl)) and a conjugate base group thereof, an alkoxysilyl group (—Si(O-alkyl)$_3$), an aryloxysilyl group (—Si(O-aryl)$_3$), a hydroxysilyl group (—Si(OH)$_3$) and a conjugate base group thereof, a phosphono group (—PO$_3$H$_2$) and a conjugate base group thereof (hereinafter, referred to as a phosphonato group), a dialkylphosphono group (—PO$_3$(alkyl)$_2$), a diarylphosphono group (—PO$_3$(aryl)$_2$), an alkylarylphosphono group (—PO$_3$(alkyl)(aryl)), a monoalkylphosphono group (—PO$_3$H(alkyl)) and a conjugate base group thereof (hereinafter, referred to as an alkylphosphonato group), a monoarylphosphono group (—PO$_3$H(aryl)) and a conjugate base group thereof (hereinafter, referred to as an arylphosphonato group), a phosphonoxy group (—OPO$_3$H$_2$) and a conjugate base group thereof (hereinafter, referred to as a phosphonatoxy group), a dialkylphosphonoxy group (—OPO$_3$(alkyl)$_2$), a diarylphosphonoxy group (—OPO$_3$(aryl)$_2$), an alkylarylphosphonoxy group (—OPO$_3$(alkyl)(aryl)), a monoalkylphosphonoxy group (—OPO$_3$H(alkyl)) and a conjugate base group thereof (hereinafter, referred to as an alkylphosphonatoxy group), a monoarylphosphonoxy group (—OPO$_3$H(aryl)) and a conjugate base group thereof (hereinafter, referred to as an arylphosphonatoxy group), a cyano group, a nitro group, an aryl group, an alkenyl group and an alkynyl group.

Specific examples of the alkyl group in the substituents include those described above, Specific examples of the aryl group in the substituents include phenyl, biphenyl, naphthyl, tolyl, xylyl, mesityl, cumenyl, fluorophenyl, chlorophenyl, bromophenyl, chloromethylphenyl, hydroxyphenyl, methoxyphenyl, ethoxyphenyl, pehnoxyphenyl, acetoxyphenyl, benzoyloxyphenyl, methylthiophenyl, phenylthiophenyl, methylaminophenyl, dimethylaminophenyl, acetylaminophenyl, carboxyphenyl, methoxycarbonylphenyl, ethoxycarbonylphenyl, phenoxycarbonylphenyl, N-phenylcarbamoylphenyl, nitrophenyl, cyanophenyl, sulfophenyl, sulfonatophenyl, phosphonophenyl and phosphonatophenyl groups. Specific examples of the alkenyl group include vinyl, 1-propenyl, 1-butenyl, cinnamyl and 2-chloro-1-ethenyl groups. Specific examples of the alkenyl group include ethynyl, 1-propynyl, 1-butynyl, trimethylsilylethynyl and phenylethynyl groups.

In the acyl group (R$^4$CO—) described above, R$^4$ represents a hydrogen atom, or the above-described alkyl group, aryl group, alkenyl group or alkynyl group.

In the substituted alkyl group, an alkylene group includes a divalent organic residue obtained by eliminating any one of hydrogen atoms on the alkyl group having from 1 to 20 carbon atoms described above, and preferably a straight chain alkylene group having from 1 to 12 carbon atoms, a branched alkylene group having from 3 to 12 carbon atoms and a cyclic alkylene group having from 5 to 10 carbon atoms. Specific preferred examples of the substituted alkyl group include chloromethyl, bromomethyl, 2-chloroethyl, trifluoromethyl, methoxymethyl, methoxyethoxyethyl, allyloxymethyl, phenoxymethyl, methylthiomethyl, tolylthiomethyl, ethylaminoethyl, diethylaminopropyl, miorpholinopropyl, acetyloxymethyl, benzoyloxymethyl, N-cyclohexylcarbamoyloxyethyl, N-phenylcarbamoyloxyethyl, acetylaminoethyl, N-methylbenzoylaminopropyl, 2-oxoethyl, 2-oxopropyl, carboxypropyl, methoxycarbonylethyl, methoxycarbonylmethyl, methoxycarbonylbutyl, ethoxycarbonylethyl, butoxycarbonylmethyl, allyloxycarbonylmethyl, benzyloxycarbonylmethyl, methoxycarbonylphenylmethyl, trichloromethylcarbonylmethyl, allyloxycarbonylbutyl, chlorophenoxycarbonylmethyl, carbamoylmethyl, N-methylcarbamoylethyl, N,N-dipropylcarbamoylmethyl, N-(methoxyphenyl)carbamoylethyl, N-methyl-N-(sulfophenyl)carbamoylmethyl, sulfopropyl, sulfobutyl, sulfonatobutyl, sulfamoylbutyl, N-ethylsulfamoylmethyl, N,N-dipropylsulfamoylpropyl, N-tolylsulfamoylpropyl, N-methyl-N-(phosphonophenyl)sulfamoyloctyl,

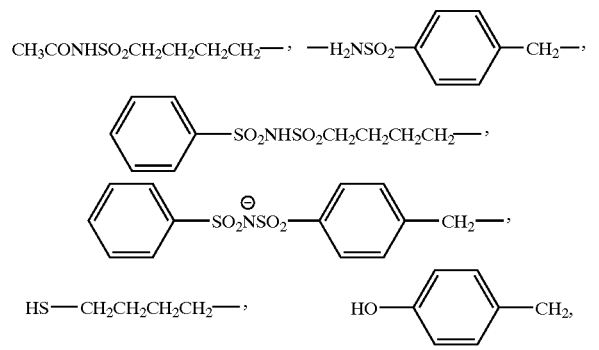

phosphonobutyl, phosphonatohexyl, diethylphosphonobutyl, diphenylphosphonopropyl, methylphosphonobutyl, methylphosphonatobutyl, tolylphosphonohexyl, tolylphosphonatohexyl, phosphonoxypropyl, phosphonatoxybutyl, benzyl, phenethyl, α-methylbenzyl, 1-methyl-1-phenylethyl, p-methylbenzyl, cinnamyl, allyl, 1-propenylmethyl, 2-butenyl, 2-methylallyl, 2-methylpropenylmethyl, 2-propynyl, 2-butynyl and 3-butynyl groups.

The aryl group includes a condensed ring of one to three benzene rings and a condensed ring of a benzene ring and a 5-membered unsaturated ring. Specific examples of the aryl group include phenyl, naphthyl, anthryl, phenanthryl, indenyl, acenaphthenyl and fluorenyl groups. A phenyl group and a naphthyl group are preferred.

The substituted aryl group is a group formed by bonding a substituent to an aryl group and includes groups having a monovalent non-metallic atomic group exclusive of a hydrogen atom, as a substituent, on the ring-forming carbon atoms of the above-described aryl group. Examples of the substituent include the above-described alkyl and substituted alkyl group and the substituents for the substituted alkyl group. Specific preferred examples of the substituted aryl group include biphenyl, tolyl, xylyl, mesityl, cumenyl, chlorophenyl, bromophenyl, fluorophenyl, chloromethylphenyl, trifluoromethylphenyl, hydroxyphenyl, methoxyphenyl, methoxyethoxyphenyl, allyloxyphenyl, phenoxyphenyl, methylthiophenyl, tolylthiophenyl, phenylthiophenyl, ethylaminophenyl, diethylaminophenyl, morpholinophenyl, acetyloxyphenyl, benzoyloxyphenyl, N-cyclohexylcarbamoyloxyphenyl, N-phenylcarbamoyloxyphenyl, acetylaminophenyl, N-methylbenzoylaminophenyl, carboxyphenyl, methoxycarbonylphenyl, allyloxycarbonylphenyl, chlorophenoxycarbonylphenyl, carbamoylphenyl, N-methylcarbamoylphenyl, N,N-dipropylcarbamoylphenyl, N-(methoxyphenyl) carbamoylphenyl, N-methyl-N-(sulfophenyl)carbamoylphenyl, sulfophenyl, sulfonatophenyl, sulfamoylphenyl, N-ethylsulfamoylphenyl, N,N-dipropylsulfamoylphenyl, N-tolylsulfamoylphenyl, N-methyl-N-(phosphonophenyl) sulfamoylphenyl, phosphonophenyl, phosphonatophenyl, diethylphosphonophenyl, diphenylphosphonophenyl, methylphosphonophenyl, methylphosphonatophenyl, tolylphosphonophenyl, tolylphosphonatophenyl, allylphenyl, 1-propenylmethylphenyl, 2-butenylphenyl, 2-methylallylphenyl, 2-methylpropenylphenyl, 2-propynylphenyl, 2-butynylphenyl and 3-butynylphenyl groups.

The alkenyl group includes that described above. The substituted alkenyl group is a group formed by replacing a hydrogen atom of the alkenyl group with a substituent. Examples of the substituent include the substituents for the substituted alkyl group described above, and the alkenyl group is that described above. Preferred examples of the substituted alkenyl group include the following groups:

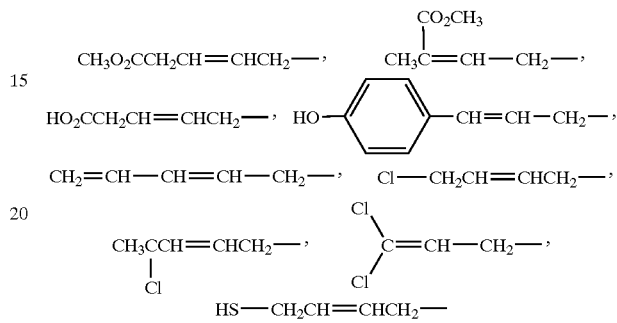

The alkynyl group includes that described above. The substituted alkynyl group is a group formed by replacing a hydrogen atom of the alkynyl group with a substituent. Examples of the substituent include the substituents for the substituted alkyl group described above, and the alkynyl group is that described above.

The heterocyclic group includes a monovalent group formed by eliminating one hydrogen atom on the hetero ring and a monovalent group (a substituted heterocyclic group) formed by further eliminating one hydrogen atom from the above-described monovalent group and bonding a substituent selected from the substituents for the substituted alkyl group described above. Preferred examples of the hetero ring are set forth below.

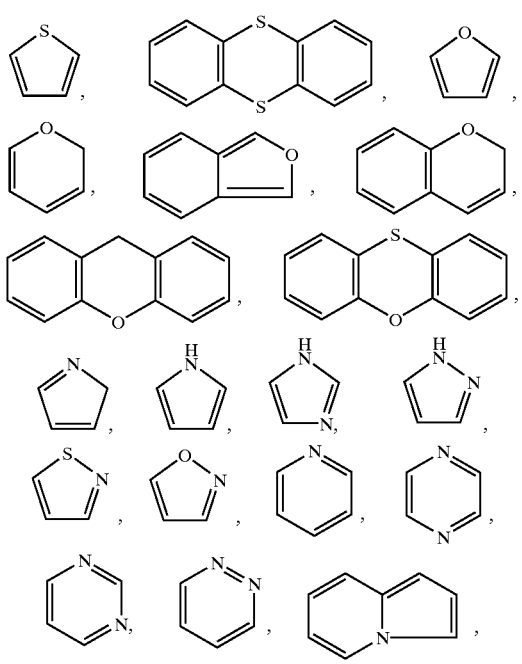

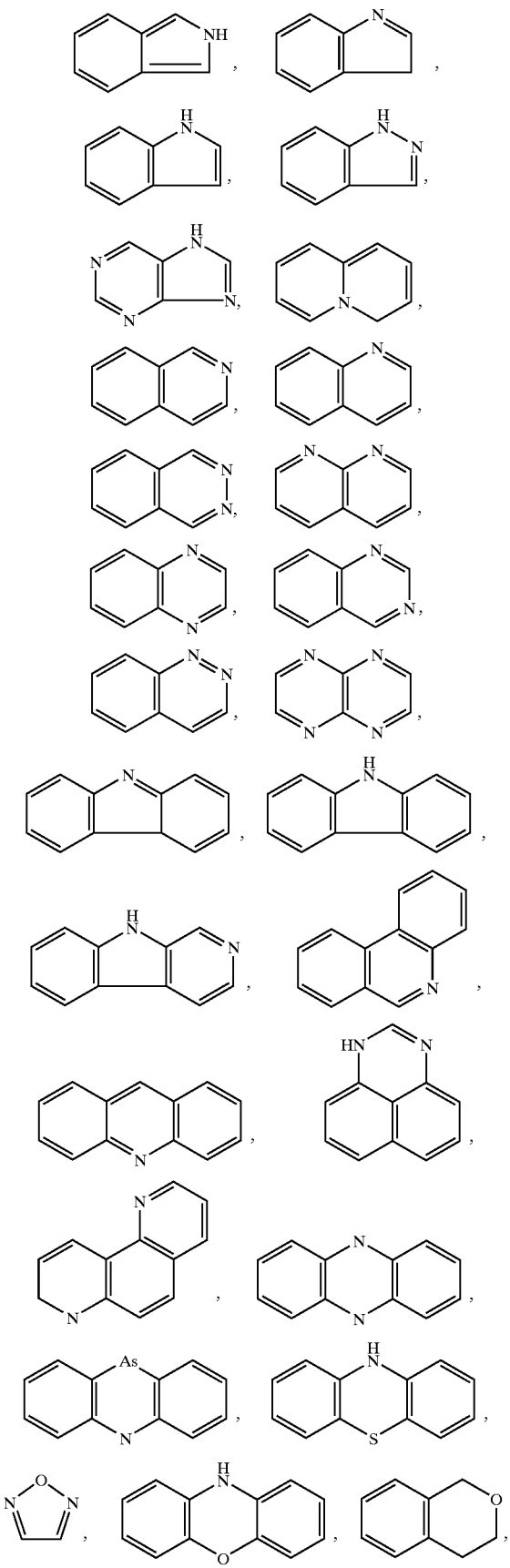

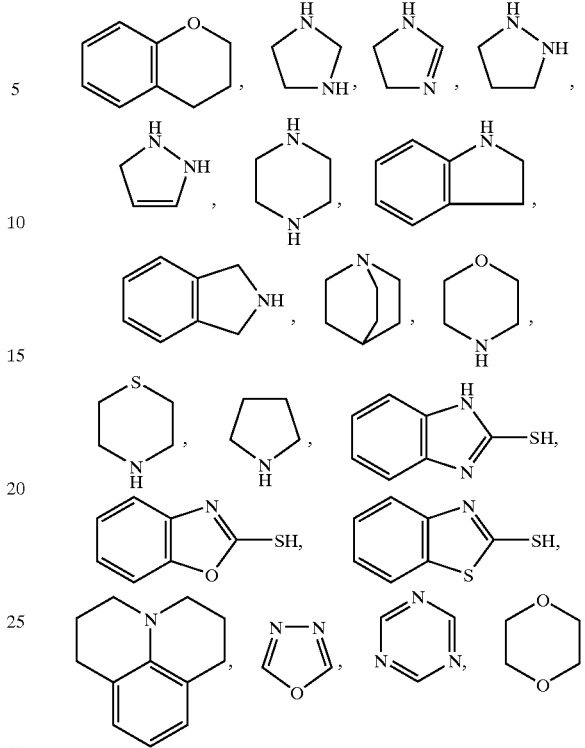

In the substituted oxy group (R⁵O—) described above, $R^5$ represents a monovalent non-metallic atomic group excusive of a hydrogen atom. Preferred examples of the substituted oxy group include an alkoxy group, an aryloxy group, an acyloxy group, a carbamoyloxy group, an N-alkylcarbamoyloxy group, an N-arylcarbamoyloxy group, an N,N-dialkylcarbamoyloxy group, an N,N-diarylcarbamoyloxy group, an N-alkyl-N-arylcarbamoyloxy group, an alkylsulfoxy group, an arylsulfoxy group, a phosphonoxy group and a phosphonatoxy group. The alkyl group and aryl group in the above-described substituted oxy group include those described for the alkyl group, substituted alkyl group, aryl group and substituted aryl group above. In an acyl group ($R^6CO$—) in the acyloxy group described above, $R^6$ represents the alkyl group, substituted alkyl group, aryl group and substituted aryl group described above. Of the substituted oxy groups, an alkoxy group, an aryloxy group, an acyloxy group and an arylsulfoxy group are more preferred. Specific preferred examples of the substituted oxy group include methoxy, ethoxy, propyloxy, isopropyloxy, butyloxy, pentyloxy, hexyloxy, dodecyloxy, benzyloxy, allyloxy, phenethyloxy, carboxyethyloxy, methoxycarbonylethyloxy, ethoxycarbonylethyloxy, methoxyethoxy, phenoxyethoxy, methoxyethoxyethoxy, ethoxyethoxyethoxy, morpholinoethoxy, morpholinopropyloxy, allyloxyethoxyethoxy, phenoxy, tolyloxy, xylyloxy, mesityloxy, cumenyloxy, methoxyphenyloxy, ethoxyphenyloxy, chlorophenyloxy, bromophenyloxy, acetyloxy, benzoyloxy, naphthyloxy, phenylsulfonyloxy, phosphonoxy and phosphonatoxy groups.

In the substituted thio group ($R^7S$—) described above, $R^7$ represents a monovalent non-metallic atomic group excusive of a hydrogen atom. Preferred examples of the substituted thio group include an alkylthio group, an arylthio group, an alkyldithio group, an aryldithio group and an acylthio group. The alkyl group and aryl group in the above-described substituted thio group include those described for the alkyl group, substituted alkyl group, aryl group and substituted aryl group above. In an acyl group ($R^6CO—$) in the acylthio group described above, $R^6$ has the same meaning as described above. Of the substituted thio groups, an alkylthio group and an arylthio group are more preferred. Specific preferred examples of the substituted thio group include methylthio, ethylthio, phenylthio, ethoxyethylthio, carboxyethylthio and methoxycarbonylthio groups.

In the substituted amino group ($R^8NH—$ or $(R^9)(R^{10})N—$) described above, $R^8$, $R^9$ and $R^{10}$ each represents a monovalent non-metallic atomic group excusive of a hydrogen atom. Preferred examples of the substituted amino group include an N-alkylamino group, an N,N-dialkylamino group, an N-arylamino group, an N,N-diarylamino group, an N-alkyl-N-arylamino group, an acylamino group, an N-alkylacylamino group, an N-arylacylamino group, a ureido group, an N'-alkylureido group, an N',N'-dialkylureido group, an N'-arylureido group, an N',N'-diarylureido group, an N'-alkyl-N'-arylureido group, an N-alkylureido group, an N-arylureido group, an N'-alkyl-N-alkylureido group, an N'-alkyl-N-arylureido group, an N',N'-dialkyl-N-alkylureido group, an N',N'-dialkyl-N-arylureido group, an N'-aryl-N-alkylureido group, an N'-aryl-N-arylureido group, an N',N'-diaryl-N-alkylureido group, an N',N'-diaryl-N-arylureido group, an N'-alkyl-N'-aryl-N-alkylureido group, an N'-alkyl-N'-aryl-N-arylureido group, an alkoxycarbonylamino group, an aryloxycarbonylamino group, an N-alkyl-N-alkoxycarbonylamino group, an N-alkyl-N-aryloxycarbonylamino group, an N-aryl-N-alkoxycarbonylamino group and an N-aryl-N-aryloxycarbonylamino group. The alkyl group and aryl group in the above-described substituted amino group include those described for the alkyl group, substituted alkyl group, aryl group and substituted aryl group above. In an acyl group ($R^6CO—$) in the acylamino group, N-alkylacylamino group or N-arylacylamino group described above, $R^6$ has the same meaning as described above. Of the substituted amino groups, an N-alkylamino group, an N,N-dialkylamino group, an N-arylamino group and an acylamino group are more preferred. Specific preferred examples of the substituted amino group include methylamino, ethylamino, diethylamino, morpholino, piperidino, pyrrolidino, phenylamino, benzoylamino and acetylamino groups.

In the substituted carbonyl group ($R^{11}—CO—$) described above, $R^{11}$ represents a monovalent non-metallic atomic group excusive of a hydrogen atom. Preferred examples of the substituted carbonyl group include an acyl group, a carboxy group, an alkoxycarbonyl group, an aryloxycarbonyl group, a carbamoyl group, an N-alkylcarbamoyl group, an N,N-dialkylcarbamoyl group, an N-arylcarbamoyl group, an N,N-diarylcarbamoyl group and an N-alkyl-N-arylcarbamoyl group. The alkyl group and aryl group in the above-described substituted carbonyl group include those described for the alkyl group, substituted alkyl group, aryl group and substituted aryl group above. Of the substituted carbonyl groups, an acyl group, a carboxy group, an alkoxycarbonyl group, an aryloxycarbonyl group, a carbamoyl group, an N-alkylcarbamoyl group, an N,N-dialkylcarbamoyl group and an N-arylcarbamoyl group are more preferred, and an acyl group, an alkoxycarbonyl group and an aryloxycarbonyl group are still more preferred. Specific preferred examples of the substituted carbonyl group include formyl, acetyl, benzoyl, carboxy, methoxycarbonyl, allyloxycarbonyl, N-methylcarbamoyl, N-phenylcarbamoyl, N,N-diethylcarbamoyl and morpholinocarbonyl groups.

In the substituted sulfinyl group ($R^{12}—SO—$) described above, $R^{12}$ represents a monovalent non-metallic atomic group excusive of a hydrogen atom. Preferred examples of the substituted sulfinyl group include an alkylsulfinyl group, an arylsulfinyl group, a sulfinamoyl group, an N-alkyl sulfinamoyl group, an N,N-dialkylsulfinamoyl group, an N-arylsulfinamoyl group, an N,N-diarylsulfinamoyl group and an N-alkyl-N-arylsulfinamoyl group. The alkyl group and aryl group in the above-described substituted sulfinyl group include those described for the alkyl group, substituted alkyl group, aryl group and substituted aryl group above. Of the substituted sulfinyl groups, an alkylsulfinyl group and an arylsulfinyl group are more preferred. Specific examples of the substituted sulfinyl group include hexylsulfinyl, benzylsulfinyl and tolylsulfinyl groups.

In the substituted sulfonyl group ($R^{13}—SO_2—$) described above, $R^{13}$ represents a monovalent non-metallic atomic group excusive of a hydrogen atom. Preferred examples of the substituted sulfonyl group include an alkylsulfonyl group and an arylsulfonyl group. The alkyl group and aryl group in the above-described substituted sulfonyl group include those described for the alkyl group, substituted alkyl group, aryl group and substituted aryl group above. Specific examples of the substituted sulfonyl group include butylsulfonyl and chlorophenylsulfonyl groups.

The sulfonato group ($—SO_3^-$) described above means a conjugate base anion group of a sulfo group ($—SO_3H$) as described above. Ordinarily, it is preferred to use together with a counter cation. Examples of the counter cation include those conventionally known, for example, various oniums (e.g., ammonium, sulfonium, phosphonium iodonium or azinium) and metal ions (e.g., $Na^+$, $K^+$, $Ca^{2+}$ or $Zn^{2+}$).

The carboxylato group ($—CO_2$) described above means a conjugate base anion group of a carboxy group ($—CO_2H$) as described above. Ordinarily, it is preferred to use together with a counter cation. Examples of the counter cation include those conventionally known, for example, various oniums (e.g., ammonium, sulfonium, phosphonium iodonium or azinium) and metal ions (e.g., $Na^+$, $K^+$, $Ca^{2+}$ or $Zn^{2+}$).

The substituted phosphono group described above means a group formed by substituting one or two hydroxy groups of a phosphono group with one or two other organic oxy groups. Preferred examples of the substituted phosphono group include a dialkylphosphono group, a diarylphosphono group, an alkylarylphosphono group, a monoalkylphosphono group and a monoarylphosphono group as described above. Of the substituted phosphono groups, a dialkylphosphono group and a diarylphosphono group are more preferred. Specific examples of the substituted phosphono group include diethylphosphono, dibutylphosphono and diphenylphosphono groups.

The phosphonato group ($—PO_3^{2-}$ or $—PO_3H^-$) described above means a conjugate base anion group of a phosphono group ($—PO_3H_2$) resulting from primary acid dissociation or secondary acid dissociation as described above. Ordinarily, it is preferred to use together with a counter cation. Examples of the counter cation include those conventionally known, for example, various oniums (e.g., ammonium, sulfonium, phosphonium iodonium or azinium) and metal ions (e.g., $Na^+$, $K^+$, $Ca^{2+}$ or $Zn^{2+}$).

The substituted phosphonato group described above means a conjugate base anion group of a group formed by substituting one hydroxy group of a phosphono group with another organic oxy group. Specific examples of the substituted phosphonato group include a conjugate base group of a monoalkylphosphono group (—PO$_3$H(alkyl)) and a conjugate base group of a monoarylphosphono group (—PO$_3$H(aryl)). Ordinarily, it is preferred to use together with a counter cation. Examples of the counter cation include those conventionally known, for example, various oniums (e.g., ammonium, sulfonium, phosphonium iodonium or azinium) and metal ions (e.g., Na$^+$, K$^+$, Ca$^{2+}$ or Zn$^{2+}$).

Now, the cyclic structure formed by combining R$^a$ and R$^b$, X$^1$ and R$^a$ or R$^b$, X$^3$ and R$^a$ or R$^b$, or Q$^1$ and R$^a$ or R$^b$ with each other is described below. An aliphatic ring formed by combining R$^a$ and R$^b$, X$^1$ and R$^a$ or R$^b$, X$^3$ and R$^a$ or R$^b$, or Q$^1$ and R$^a$ or R$^b$ with each other includes a 5-membered, 6-membered, 7-membered and 8-membered aliphatic rings, and preferably a 5-membered and 6-membered aliphatic rings. The aliphatic ring may have one or more substituents (examples thereof include the substituents for the substituted alkyl group described above) on one or more carbon atoms forming the ring. Also, a part of the aliphatic ring-forming carbon atoms may be replaced by hetero atom(s) (examples thereof include an oxygen atom, a sulfur atom and a nitrogen atom). Further, a part of the aliphatic ring may also form a part of an aromatic ring.

Specific examples of the compound having a structure represented by formula (I), (II) or (III) are set forth below, but the present invention should not be construed as being limited thereto.

Examples of the compound having a structure represented by formula (I)

TABLE 1

Group A

| No. | X$^3$ | Q$^1$ |
|---|---|---|
| A-1 | (benzothiazol-2-ylthio) | CO$_2$CH$_3$ |
| A-2 | " | CO$_2$C$_2$H$_5$ |
| A-3 | " | CO$_2$(n)C$_4$H$_9$ |
| A-4 | " | CO$_2$(n)C$_{12}$H$_{25}$ |
| A-5 | " | CO$_2$-benzyl |
| A-6 | " | CO$_2$-cyclohexyl |
| A-7 | " | CO$_2$-allyl |
| A-8 | " | CO$_2$-(4-tert-butylphenyl) |
| A-9 | " | C≡N |
| A-10 | " | CONH-phenyl |
| A-11 | " | CONH(n)C$_6$H$_{13}$ |
| A-12 | " | CON(benzyl)$_2$ |
| A-13 | " | COS(n)C$_{12}$H$_{25}$ |
| A-14 | " | CO$_2$H |

TABLE 1-continued

Group A

[Structure: CH2=C(Q1)-CH2-X3]

| No. | X³ | Q¹ |
|-----|----|----|
| A-15 | benzothiazol-2-ylthio | $CO_2^{\ominus} Na^{\oplus}$ |
| A-16 | " | $CO_2^{\ominus}((n)C_4H_9)_4N^{\oplus}$ |
| A-17 | benzoxazol-2-ylthio | $CO_2CH_3$ |
| A-18 | 3,3-dimethylindol-2-ylthio | " |
| A-19 | 5-chlorobenzothiazol-2-ylthio | " |
| A-20 | 4,5-diphenylthiazol-2-ylthio | " |
| A-21 | 5-(NHCO(n)C₄H₉)-benzoxazol-2-ylthio | " |
| A-22 | 5-(NHCO(n)C₁₂H₂₅)-benzothiazol-2-ylthio | " |
| A-23 | benzimidazol-2-ylthio | " |
| A-24 | morpholino | " |
| A-25 | 4-(CO(n)C₆H₁₃)piperazin-1-yl | " |

TABLE 1-continued

Group A $$\underset{Q^1}{\overset{X^3}{\diagdown}}$$

| No. | X³ | Q¹ |
|---|---|---|
| A-26 | (pyrrolidine) | " |
| A-27 | (isoindoline) | " |
| A-28 | (carbazole) | " |
| A-29 | (pyridinium) | " |

Examples of the compound having a structure represented by formula (II)

TABLE 2

Group B $$\underset{CN\ \ NC}{\overset{Z^2}{\diagup\diagdown}}$$

| No. | Z² |
|---|---|
| B-1 | O—(CH₂)₆—O |
| B-2 | O—(CH₂)₁₂—O |
| B-3 | O—CH₂CH₂—O—CH₂CH₂—O—CH₂CH₂—O |
| B-4 | O—CH₂CH₂—(O—CH₂CH₂)₂₁—O (average number) |
| B-5 | O—CH₂—C₆H₄—CH₂—O |

TABLE 2-continued

Group B

[structure: CH2=C(CN)-CH2-Z²-CH2-C(CN)=CH2]

| No. | Z² |
|---|---|
| B-6 | −O−(p-C₆H₄)−O− |
| B-7 | −OCO−(CH₂)₃−COO− |
| B-8 | −OCO−(CH₂)₈−COO− |
| B-9 | −OCO−(p-C₆H₄)−COO− |
| B-10 | −OCO−CH₂−(p-C₆H₄)−CH₂−COO− |
| B-11 | −OCO−(1,4-cyclohexylene)−COO− |
| B-12 | −OCONH−(CH₂)₆−NHCOO− |
| B-13 | −OCONH−(m-C₆H₄)−NHCOO− |
| B-14 | −OCONH−(p-C₆H₄)−C(CH₃)₂−(p-C₆H₄)−NHCOO− |
| B-15 | −OSO₂−(CH₂)₄−SO₂O− |
| B-16 | −OSO₂−(2,3,5,6-tetramethyl-1,4-phenylene)−SO₂O− |
| B-17 | −OCO−(CH₂)₃−COO−(CH₂)₄−OCO−(CH₂)₃−COO− |
| B-18 | −OCO−(CH₂)₃−CONH−(CH₂)₆−NHCO−(CH₂)₃−COO− |
| B-19 | −OCO−CH₂CH₂−CO−[O−CH₂CH₂−OCO−(p-C₆H₄)−CO−]₂₀−O−CH₂CH₂−OCO−CH₂CH₂−COO−  (average number) |

TABLE 2-continued

Group B

[structure: CH2=C(CN)-CH2-Z²-CH2-C(CN)=CH2]

| No. | Z² |
|---|---|
| B-20 | OCO-CH2-CH2-CONH-(CH2)4-O |
| B-21 | OCO-(CH2)4-O |
| B-22 | OCO-(CH2)4-OCO |
| B-23 | OCO-CH2CH2-OCO |
| B-24 | OCO-(CH2)4-OCO |
| B-25 | OCO-(CH2)5-OCO |
| B-26 | S-(CH2)6-S |
| B-27 | NHCO-(CH2)6-CONH |
| B-28 | (CH3)N-(CH2)6-N(CH3) |
| B-29 | 1,4-phenylene with -N(CH3)-CO- on each side |
| B-30 | NHCOO-(CH2)4-OCONH |
| B-31 | naphthalene-1,5-disulfonamide (HNO2S- and -SO2NH) |

Examples of the compound having a structure represented by formula (III)
TABLE 3
Group C
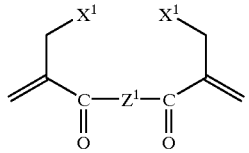
| No. | X¹ | Z¹ |
|---|---|---|
| C-1 | OCOCH$_3$ | 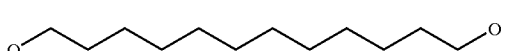 |
| C-2 | OCOCH$_3$ | 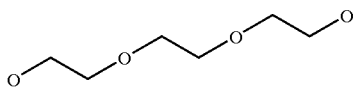 |
| C-3 | OCOCH$_3$ | 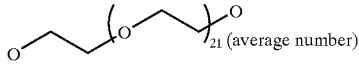 |
| C-4 | OCOCH$_3$ | 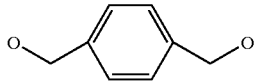 21 (average number) |
| C-5 | OCOCH$_3$ |  |
| C-6 | OCOCH$_3$ | 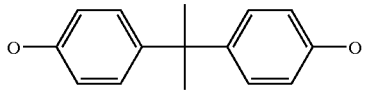 |
| C-7 | OCOCH$_3$ | 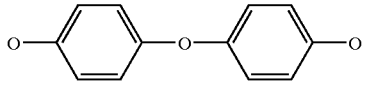 |
| C-8 | OCOCH$_3$ | 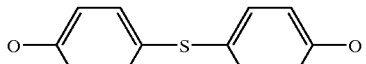 |
| C-9 | OCH$_3$ | 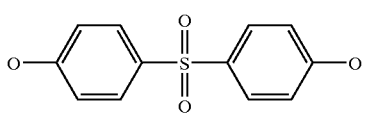 |
| C-10 | 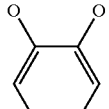 | 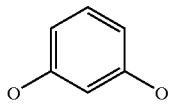 |
| C-11 | OCOC$_2$H$_5$ | |
| C-12 | OCOC$_2$H$_5$ | |

TABLE 3-continued
Group C
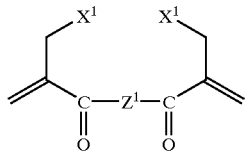
| No. | X¹ | Z¹ |
|---|---|---|
| C-13 | OCOC₂H₅ | 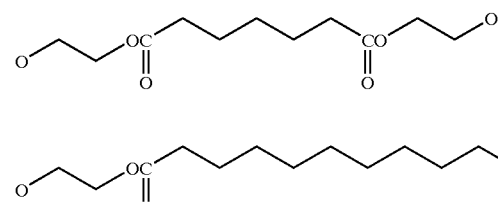 |
| C-14 | OCOCH₃ | 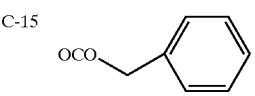 |
| C-15 | 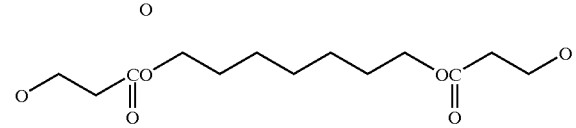 | 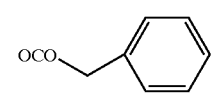 |
| C-16 | 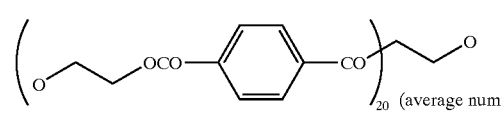 | 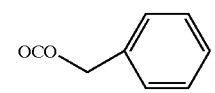 (average number) |
| C-17 | 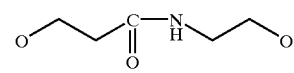 | 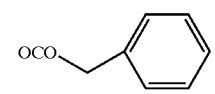 |
| C-18 | 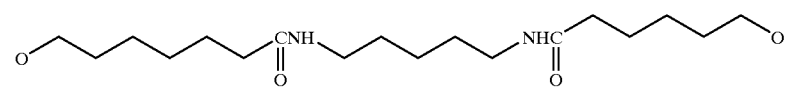 | 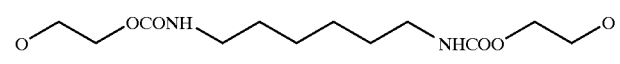 |
| C-19 | OCOCH₃ | 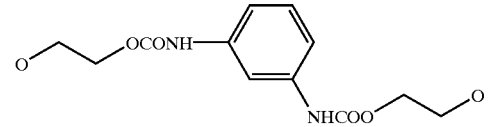 |
| C-20 | OCOCH₃ | 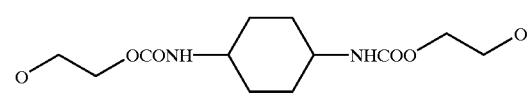 |
| C-21 | OCO(n)Pr | 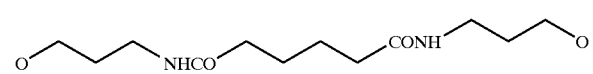 |
| C-22 | OCO(n)Pr | 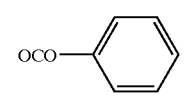 |
| C-23 | 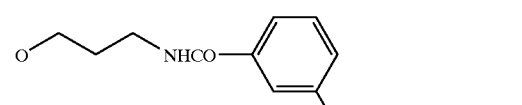 | 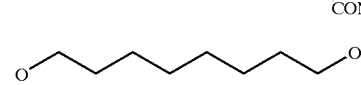 |
| C-24 | SCH₃ | 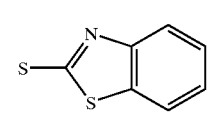 |
| C-25 | 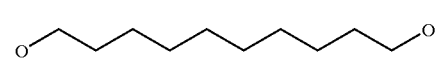 | |

TABLE 3-continued

Group C

[Structure: X¹—CH₂—C(=CH₂)—C(=O)—Z¹—C(=O)—C(=CH₂)—CH₂—X¹]

| No. | X¹ | Z¹ |
|---|---|---|
| C-26 | SCOCH₃ | —O—(CH₂)₇—O— |
| C-27 | OSO₂CH₃ | —O—CH₂—C(CH₂OH)(CH₂OH)—CH₂—O— |
| C-28 | OSO₂—C₆H₄—CH₃ (p-tolyl) | —O—C₆H₃(Cl)—O— (2-chloro-1,4-phenylenedioxy) |
| C-29 | N(CH₃)₂ | —O—C₆H₄—O— (1,4-phenylenedioxy) |
| C-30 | morpholino (N-linked) | —O—(CH₂)₄—O— |
| C-31 | piperidino (N-linked) | —NHSO₂—C₆H₄—SO₂NH— (m-phenylene) |
| C-32 | F | —O—(CH₂)₄—O— |
| C-33 | NHCOCH₃ | piperazine-1,4-diyl |
| C-34 | NHSO₂—C₆H₄— | —HN—(CH₂)₄—NH— |
| C-35 | NHCO₂—C₆H₅ | —NH—CH₂CH₂—O—CH₂CH₂—O—CH₂CH₂—NH— |

Examples of the compound having a structure represented by formula (II)

TABLE 4

Group D

[structure: $Z^2$ branching with two =CH$_2$ groups and COX$^2$ / $^2$XOC substituents]

| No. | X² | Z² |
|-----|-----|-----|
| D-1 | OCH₃ | O–(CH₂)₆–O |
| D-2 | OCH₃ | O–(CH₂)₁₂–O |
| D-3 | OC₂H₅ | O–CH₂CH₂–O–CH₂CH₂–O–CH₂CH₂–O |
| D-4 | OC₂H₅ | O–CH₂CH₂–(O–CH₂CH₂)₂₁–O (average number) |
| D-5 | O–CH₂–CH=CH₂ | O–CH₂–(p-C₆H₄)–CH₂–O |
| D-6 | O–CH₂–C₆H₅ | O–(p-C₆H₄)–O |
| D-7 | OCH₃ | OCO–(CH₂)₄–COO |
| D-8 | OCH₃ | OCO–(CH₂)₈–COO |
| D-9 | O(n)C₄H₉ | OCO–(p-C₆H₄)–COO |
| D-10 | O(n)C₄H₉ | OCO–CH₂–(p-C₆H₄)–CH₂–COO |
| D-11 | O–CH₂CH₂–OCH₃ | OCO–(1,4-C₆H₁₀)–COO |
| D-12 | O–CH₂CH₂–N(CH₃)₂ | OCONH–(CH₂)₆–NHCOO |
| D-13 | OCH₃ | OCONH–(m-C₆H₄)–NHCOO |
| D-14 | OCH₃ | OCONH–(p-C₆H₄)–C(CH₃)₂–(p-C₆H₄)–NHCOO |

TABLE 4-continued

Group D $$\text{CH}_2=\text{C}(\text{COX}^2)\text{-CH}_2\text{-Z}^2\text{-CH}_2\text{-C}(\text{COX}^2)=\text{CH}_2$$

| No. | $X^2$ | $Z^2$ |
|---|---|---|
| D-15 | $OCH_3$ | $OSO_2\text{-(CH}_2)_n\text{-}SO_2O$ |
| D-16 | $O(n)C_{12}H_{25}$ | (trimethylbenzene-1,3-disulfonate: $OSO_2$–Ar(Me)$_3$–$SO_2O$) |
| D-17 | $OCH_3$ | $OCO\text{-(CH}_2)_4\text{-}COO\text{-(CH}_2)_4\text{-}OCO\text{-(CH}_2)_4\text{-}COO$ |
| D-18 | $OCH_3$ | $OCO\text{-(CH}_2)_4\text{-}CONH\text{-(CH}_2)_6\text{-}NHCO\text{-(CH}_2)_4\text{-}COO$ |
| D-19 | $OCH_3$ | $OCO\text{-CH}_2\text{CH}_2\text{-}CO(\text{-}O\text{CH}_2\text{CH}_2\text{-}OCO\text{-}C_6H_4\text{-}CO\text{-})_{20}\text{-}OCH_2CH_2\text{-}OCO\text{-}CH_2CH_2\text{-}COO$ (average number) |
| D-20 | $OC_2H_5$ | $OCO\text{-CH}_2CH_2\text{-}CONH\text{-(CH}_2)_4\text{-}O$ |
| D-21 | $OCH_3$ | $OCO\text{-(CH}_2)_4\text{-}O$ |
| D-22 | $SCH_3$ | $OCO\text{-(CH}_2)_4\text{-}OCO$ |
| D-23 | phenyl-S | $OCO\text{-CH}_2CH_2\text{-}OCO$ |
| D-24 | 5-chloro-benzothiazol-2-yl-S | $OCO\text{-CH}_2CH_2\text{-}OCO$ |
| D-25 | $N(CH_3)(C_2H_5)$ | $OCO\text{-(CH}_2)_4\text{-}OCO$ |
| D-26 | morpholino | $OCO\text{-(CH}_2)_4\text{-}OCO$ |
| D-27 | $NH(n)C_{12}H_{25}$ | $OCO\text{-(CH}_2)_4\text{-}OCO$ |
| D-28 | $OCH_3$ | $S\text{-(CH}_2)_6\text{-}S$ |
| D-29 | $O\text{-CH}_2CH_2\text{-}OH$ | $S\text{-(CH}_2)_6\text{-}S$ |

TABLE 4-continued

Group D structure: CH2=C(COX²)-CH2-Z²-CH2-C(=CH2)-COX²

| No. | X² | Z² |
|---|---|---|
| D-30 | -O-(CH2)4-OCOCH3 | -NHCO-(CH2)5-CONH- |
| D-31 | OCH3 | -N(CH3)-(CH2)6-N(CH3)- |
| D-32 | OCH3 | -N(CH3)CO-C6H4-CON(CH3)- |
| D-33 | OCH3 | -NHCOO-(CH2)4-OCONH- |
| D-34 | OCH3 | 1,5-naphthalene-bis(SO2NH-) |
| D-35 | OCH3 | -OCO-CH2-O-CH2-CH2-O-CH2-OCO- |
| D-36 | OCH3 | -OCO-CH2CH2-S-CH2CH2-COO- |
| D-37 | OCH3 | -OCO-(CH2)7-COO- |
| D-38 | OCH3 | -OCO-(CH2)8-COO- |
| D-39 | OCH3 | -OCO-(CH2)6-COO- |
| D-40 | OCH3 | -OCO-(CH2)3-OCONH-(CH2)6-NHCOO-(CH2)3-COO- |
| D-41 | OCH3 | -OCO-(CH2)3-OCO-(CH2)4-COO-(CH2)3-COO- |
| D-42 | OCH3 | -OCO-(CH2)3-OCONH-(CH2)4-NHCOO-(CH2)3-COO- |
| D-43 | OCH3 | piperidine-4-COO-(CH2)6-OCO-piperidine-4 |
| D-44 | OCH3 | piperidine-4-OCO-(CH2)6-COO-piperidine-4 |

Examples of the compound having a structure represented by formula (III)

TABLE 5

Group E $$\left( \begin{array}{c} X^1 \\ | \\ CH_2 \\ \| \\ C-C(=O)- \end{array} \right)_n Z^1 \quad (n \geq 3)$$

| No. | X¹ | Z¹ |
|---|---|---|
| E-1 | OCOCH₃ | 1,3,5-trioxybenzene |
| E-2 | OCH₃ | tetrakis(4-oxyphenyl)methane-type (tris(4-oxyphenyl)(4-oxyphenyl)methane) |
| E-3 | OCOCH₃ | pentaerythritol triester (with one OCOCH₃) |
| E-4 | OCOCH₃ | pentaerythritol tetraester |
| E-5 | OCOCH₃ | 1,3,5-tris(2-oxyethoxycarbonyl)benzene |
| E-6 | OCH₂CH=CH₂ | 1,3,5-tris(2-oxyethoxycarbonyl)benzene |
| E-7 | OCOCH₃ | 2,4,6-tris(4-oxybutoxy)-1,3,5-triazine |

TABLE 5-continued

Group E $$\left( \begin{array}{c} X^1 \\ | \\ CH_2 \\ \parallel \\ CH_2=C-C-Z^1 \\ \parallel \\ O \end{array} \right)_n \quad (n \geq 3)$$

| No. | X¹ | Z¹ |
|---|---|---|
| E-8 | OCOCH₃ | (pentaerythritol tetrakis(2-hydroxyethyl) ester structure) |
| E-9 | OCOCH₃ | (dipentaerythritol hexa-substituted structure) |
| E-10 | OCOCH₃ | (dipentaerythritol penta-substituted with one OH) |
| E-11 | SCH₃ | (pentaerythritol tetra-substituted) |
| E-12 | Cl | (pentaerythritol tetra-substituted) |
| E-13 | Br | (pentaerythritol tetra-substituted) |
| E-14 | $-\overset{+}{N}(CH_3)_3 \ Cl^-$ | (1,3,5-trisubstituted benzene) |
| E-15 | $-N(CH_3)_2$ | (1,3,5-trisubstituted benzene) |
| E-16 | (morpholino) | (trimethylolpropane-type tri-substituted) |

TABLE 5-continued

Group E $$\left( \begin{array}{c} X^1 \\ | \\ CH_2 \\ | \\ C-Z^1 \\ \| \\ O \end{array} \right)_n \quad (n \geq 3)$$

| No. | X¹ | Z¹ |
|---|---|---|
| E-17 | OCO(n)C₁₂H₂₅ | HN–CH₂–CH(CH₂NH)–CH₂–NH (tris-aminomethyl) |
| E-18 | –S–C₆H₅ | HN–CH₂CH₂–N(–CH₂CH₂–NH)–CH₂CH₂–NH |
| E-19 | –SO₂–C₆H₅ | pentaerythritol-type (O–, O–, O–, OH) |
| E-20 | –OSO₂–C₆H₄–CH₃ | pentaerythritol-type (four O–) |
| E-21 | NHCOCH₃ | pentaerythritol-type (four O–) |
| E-22 | –NHSO₂–C₆H₄–CH₃ | pentaerythritol-type (four O–) |
| E-23 | –O–CH(CH₃)–OC₂H₅ | pentaerythritol-type (four O–) |
| E-24 | –O–C(CH₃)₃ | pentaerythritol-type (four O–) |
| E-25 | OH | pentaerythritol tetrakis(3-mercaptopropionate)-type: C(CH₂–OCO–CH₂CH₂–S–)₄ |
| E-26 | OH | N–(CH₂)₄–N |

Examples of the compound having a structure represented by formula (II)
TABLE 6
Group F
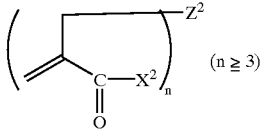
($n \geq 3$)
| No. | $X^2$ | $Z^2$ |
|---|---|---|
| F-1 | OH | 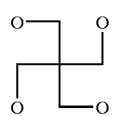 |
| F-2 | OCH$_3$ | 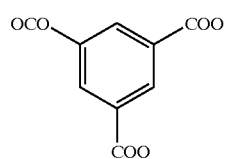 |
| F-3 | OCH$_3$ | 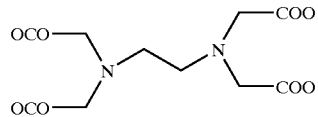 |
| F-4 | OCH$_3$ | 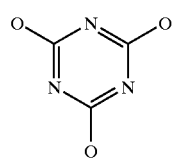 |
| F-5 | OC$_2$H$_5$ | 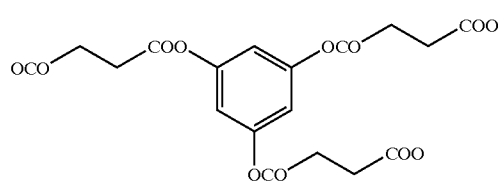 |
| F-6 | OCH$_3$ | 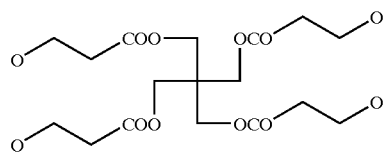 |
| F-7 | OCH$_3$ | 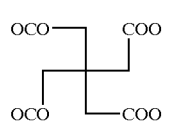 |
| F-8 | O(n)C$_3$H$_7$ | |

TABLE 6-continued

Group F $$\left( \underset{O}{\underset{\parallel}{C}}\underset{X^2}{\overset{Z^2}{\diagup}} \right)_n \quad (n \geq 3)$$

| No. | $X^2$ | $Z^2$ |
|---|---|---|
| F-9 | $N(CH_3)_2$ | benzene-1,3,5-triyl tri(OCO/COO) |
| F-10 | $O(n)C_{12}H_{25}$ | benzene-1,3,5-triyl tri(OCO/COO) |
| F-11 | NH-phenyl | benzene-1,3,5-triyl tri(OCO/COO) |
| F-12 | $NH-(n)C_4H_9$ | benzene-1,2,4,5-tetrayl tetra(OCO/COO) |
| F-13 | Cl | benzene-1,3,5-triyl tri(OCO/COO) |
| F-14 | $O^{\ominus} Na^{\oplus}$ | benzene-1,3,5-triyl tri(OCO/COO) |
| F-15 | $^{\ominus}O-CH_2CH_2CH_2-N^{\oplus}(n-C_4H_9)_3$ | benzene-1,3,5-triyl tri(OCO/COO) |

TABLE 6-continued
Group F
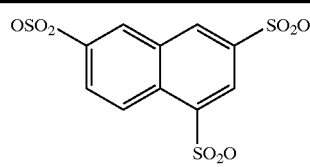
| No. | $X^2$ | $Z^2$ |
|---|---|---|
| F-16 | $OCH_3$ | 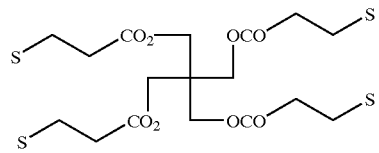 |
| F-17 | $OCH_3$ | 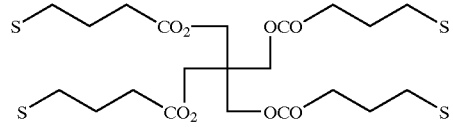 |
| F-18 | $OCH_3$ |  |
| F-19 | 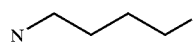 | 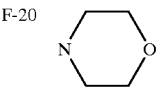 |
| F-20 | 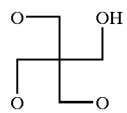 | 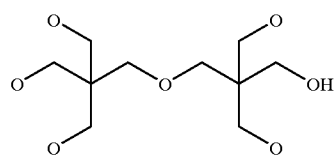 |
| F-21 | $OCH_3$ | 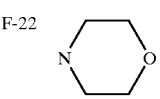 |
| F-22 |  | 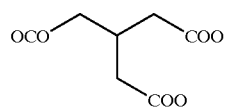 |
| F-23 | $OCH_3$ | 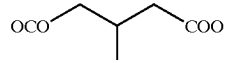 |
| F-24 | " | 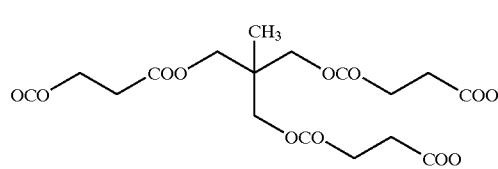 |
| F-25 | " |  |

TABLE 6-continued
Group F
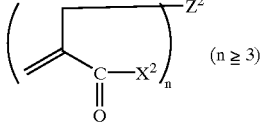
(n ≥ 3)
| No. | X² | Z² |
|---|---|---|
| F-26 | " | 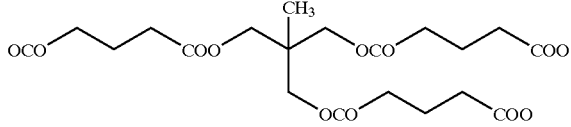 |
| F-27 | " | 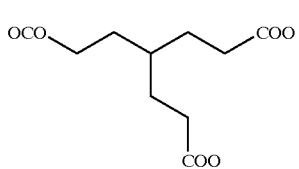 |
| F-28 | " | 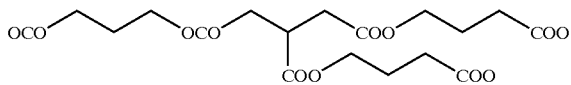 |
| F-29 | " | 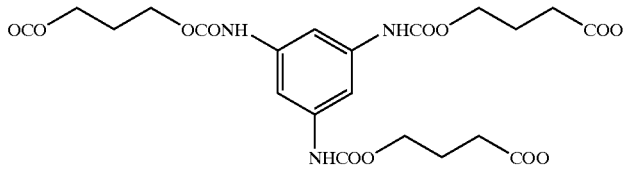 |
| F-30 | " | 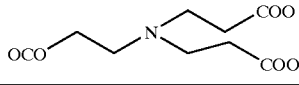 |
| F-31 | " | 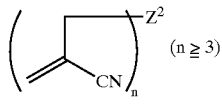 |
Examples of the compound having a structure represented by formula (II)
TABLE 7
Group G
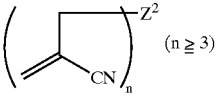 (n ≥ 3)
| No. | Z² |
|---|---|
| G-1 | 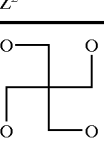 |
TABLE 7-continued
Group G
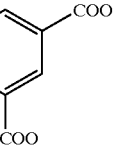 (n ≥ 3)
| No. | Z² |
|---|---|
| G-2 | 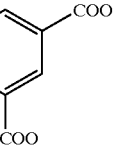 |
| G-3 | 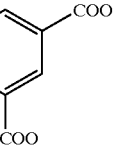 |

TABLE 7-continued

Group G: structure with $Z^2$, $CN$, $n \geq 3$

| No. | $Z^2$ |
|---|---|
| G-4 | (OCO-CH2)2N-CH2CH2-N(CH2-COO)2 structure |
| G-5 | 1,3,5-triazine-2,4,6-trione (cyanuric acid) |
| G-6 | 1,3,5-tris(OCO-CH2CH2-COO) benzene |
| G-7 | tetrakis(OCO-CH2CH2-O) methane (pentaerythritol tetraester) |
| G-8 | C(CH2-OCO)2(CH2-COO)2 |
| G-9 | benzene-1,2,4,5-tetrayl tetra(OCO...COO) |
| G-10 | CH3-C(CH2-O-CH2CH2-OCO)(CH2-O-CH2CH2-CO2)2 |
| G-11 | CH(CH2-OCO)(CH2-CO2)(CH2-CO2) |
| G-12 | naphthalene-1,3,6-triyl tris(SO2O-/OSO2) |
| G-13 | C(CH2-CO2-CH2CH2-S)2(CH2-OCO-CH2CH2-S)2 |
| G-14 | C(CH2-CO2-CH2CH2CH2-S)2(CH2-OCO-CH2CH2CH2-S)2 |
| G-15 | H3C-N(CH3)-CH2CH2CH2CH2-N(CH3)-CH3 |
| G-16 | pentaerythritol (C(CH2-O)3(CH2-OH)) |
| G-17 | dipentaerythritol with OH |
| G-18 | 1,4-diazoniabicyclo type with 2 Cl⁻ |

Examples of other compounds

Group J

| No. | Structure |
|---|---|
| J-1 | bis[2-(OCO(n)C4H9)-1-methyl methylene] with CO2-(CH2)6-OCO linker |
| J-2 | bis[2-(OCOCH3)-1-methyl methylene] with CO2-(CH2)6-OCO linker |
| J-3 | bis[2-(OCOCH3)-1,1-dimethyl methylene] with CO2-(CH2)4-OCO linker |

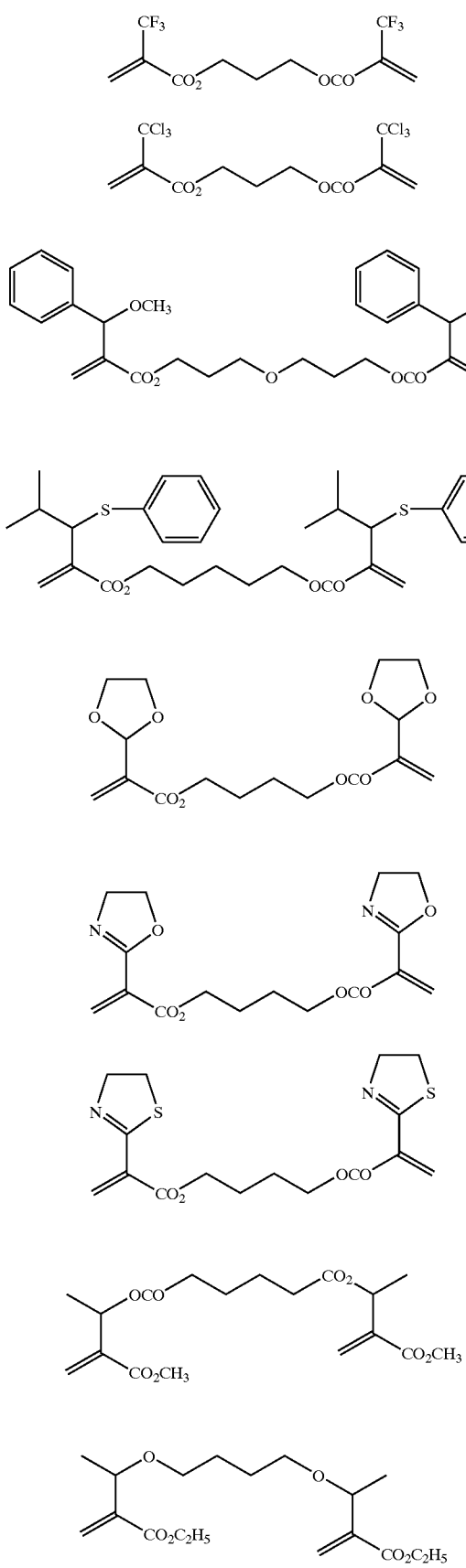
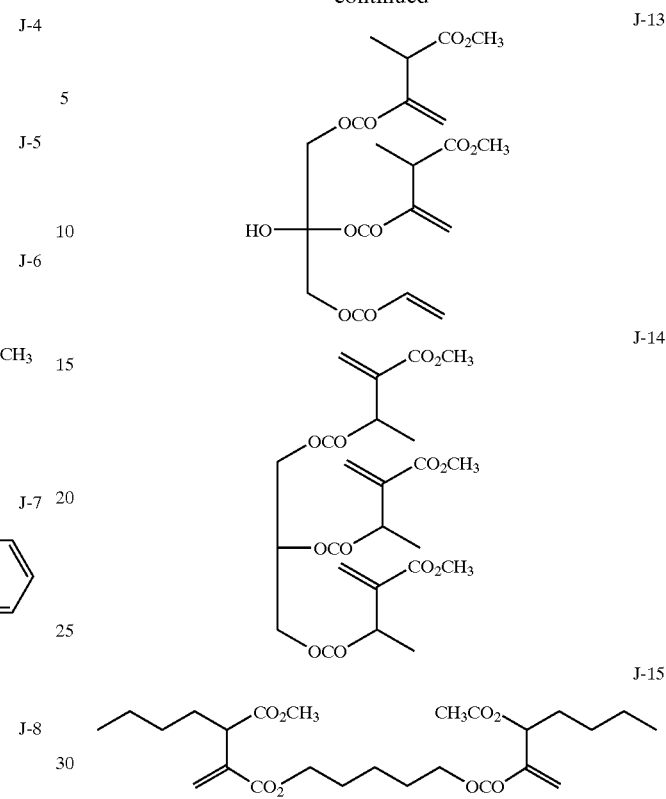

A photopolymerizable composition containing the radical polymerizable compound according to the present invention is widely applied to known uses of photosetting resins without any particular restriction, in addition to the use of lithographic printing plate for scanning exposure. For instance, the liquid photopolymerizable composition further containing a cation polymerizable compound, if desired, is used as a material for stereolithography having high sensitivity. The photopolymerizable composition is used as a material for holography utilizing the change of refractive index due to photopolymerization. It is -also applied to various transfer materials (for example, a peeling type photosensitive material or a toner development type photosensitive material) utilizing the change of adhesion on the surface. Further, it is applied to photocuring of microcapsules. Moreover, it is applied to the production of electronic materials such as photoresists, and photosetting resin materials, for example, ink, paint and adhesives.

The present invention will be described in greater detail with reference to the following examples, but the present invention should not be construed as being limited thereto.

Synthesis of compound having the structure represented by formula (I), (II) or (III) according to the present invention The compound having a structure represented by formula (I), (II) or (III) can be easily synthesized using a corresponding compound having an acryl group according to methods described in *Secchaku no Gijutsu*, Vol. 14, No. 4 (the consecutive number of volumes: 37), page 2, published by Nippon Secchaku Gakkai (1995).

SYNTHESIS EXAMPLE 1

Synthesis of Compound A-1

To a mixture of 0.1 mol of 2-mercaptobenzothiazole, 0.1 mol of methyl 2-(bromomethyl)acrylate and 100 ml of acetone in a flask was dropwise added 0.1 mol of triethylamine under cooling with ice over a period of one hour, and temperature of the mixture was returned to room temperature, followed by stirring for 2 hours. To the mixture was added 300 ml of water, and the mixture was stirred to deposit crystals. The crystals were collected by filtration and dried to obtain Compound A-1 in a yield of 90%. The melting point thereof was 124.0° C. The structure of the compound was confirmed by NMR, MASS and IR.

SYNTHESIS EXAMPLE 2

Synthesis of Compound A-14

To a mixture of 0.1 mol of 2-mercaptobenzothiazole, 0.1 mol of 2-(bromomethyl)acrylic acid and 100 ml of acetone in a flask was dropwise added 0.1 mol of triethylamine under cooling with ice over a period of one hour, and temperature of the mixture was returned to room temperature, followed by stirring for 2 hours. To the mixture was added 300 ml of water, and a pH of the mixture was adjusted to 3 or below to deposit crystals. The crystals were collected by filtration and dried to obtain Compound A-14 in a yield of 90%. The melting point thereof was more than 200° C. The structure of the compound was confirmed by NMR, MASS and IR.

SYNTHESIS EXAMPLE 3

Synthesis of Compound B-8

To a mixture of 0.1 mol of 2-(hydroxymethyl) acrylonitrile, 0.1 mol of triethylamine and 100 ml of acetone in a flask was dropwise added 0.05 mol of undecanoic dichloride under cooling with ice over a period of one hour, and temperature of the mixture was returned to room temperature, followed by stirring for 2 hours. To the mixture was added 300 ml of water, followed by stirring and the mixture was extracted with ethyl acetate. The extract was dried on magnesium sulfate and filtered. The filtrate was sufficiently concentrated under a reduced pressure to obtain Compound B-8 as a waxy solid in a yield of 80%. The structure of the compound was confirmed by NMR, MASS and IR.

SYNTHESIS EXAMPLE 4

Synthesis of Compound C-1

To a mixture of 0.75 mols of 1,6-hexanediol diacrylate, 1.0 mol of a 37% aqueous solution of formaldehyde and 100 ml of tetrahydrofuran in a flask was added 0.135 mols of DABCO, followed by stirring for 24 hours. To the reaction mixture was added a mixture of 40 ml of 1 N hydrochloric acid and 200 ml of water, and the mixture was extracted with ethyl acetate. The extract was dried on magnesium sulfate and filtered. To the filtrate was added 1.0 mol of triethylamine and then added dropwise 1.0 mol of acetic chloride under cooling with ice over a period of one hour. Temperature of the mixture was returned to room temperature, followed by stirring for 2 hours. To the mixture was added 300 ml of water, followed by stirring, and the mixture was extracted again with ethyl acetate. The extract was dried on magnesium sulfate and filtered. The filtrate was sufficiently concentrated under a reduced pressure, separated by silica gel chromatography (hexane/ethyl acetate=9/1) and concentrated under a reduced pressure to obtain Compound C-1 as colorless oil in a yield of 25%. The structure of the compound was confirmed by NMR, MASS and IR.

SYNTHESIS EXAMPLE 5

Synthesis of Compound D-7

To a mixture of 0.05 mols of adipic acid, 0.1 mol of triethylamine and 100 ml of acetone in a flask was dropwise added 0.1 mol of methyl 2-(bromomethyl)acrylate at room temperature over a period of one hour, followed by stirring for 2 hours. To the mixture was added 300 ml of water, and the mixture was stirred to deposit crystals. The crystals were collected by filtration and dried to obtain Compound D-7 in a yield of 90%. The melting point thereof was 61.0° C. The structure of the compound was confirmed by NMR, MASS and IR.

SYNTHESIS EXAMPLE 6

Synthesis of Compound D-35

To a mixture of 0.05 mols of 3,6-dioxaoctanedicarboxylic acid, 0.1 mol of triethylamine and 100 ml of acetone in a flask was dropwise added 0.1 mol of methyl 2-(bromomethyl)acrylate at room temperature over a period of one hour, followed by stirring for 2 hours. To the mixture was added 300 ml of water, followed by stirring and the mixture was extracted with ethyl acetate. The extract was dried on magnesium sulfate and filtered. The filtrate was sufficiently concentrated under a reduced pressure to obtain Compound D-35 as a semi-solid at room temperature in a yield of 60%. The structure of the compound was confirmed by NMR, MASS and IR.

SYNTHESIS EXAMPLE 7

Synthesis of Compound E-4

To a mixture of 0.375 mols of a pentaerythritol tetraacrylate, 1.0 mol of a 37% aqueous solution of formaldehyde and 100 ml of tetrahydrofuran in a flask was added 0.135 mols of DABCO, followed by stirring for 24 hours. To the reaction mixture was added a mixture of 40 ml of 1 N hydrochloric acid and 200 ml of water, and the mixture was extracted with ethyl acetate. The extract was dried on magnesium sulfate and filtered. To the filtrate was added 1.0 mol of triethylamine and then added dropwise 1.0 mol of acetic chloride under cooling with ice over a period of one hour. Temperature of the mixture was returned to room temperature, followed by stirring for 2 hours. To the mixture was added 300 ml of water, followed by stirring, and the mixture was extracted again with ethyl acetate. The extract was dried on magnesium sulfate and filtered. The filtrate was sufficiently concentrated under a reduced pressure, separated by silica gel chromatography (hexane/ethyl acetate=9/1) and concentrated under a reduced pressure to obtain Compound E-4 as colorless oil in a yield of 20%. The structure of the compound was confirmed by NMR, MASS and IR.

SYNTHESIS EXAMPLE 8

Synthesis of Compound F-24

To a mixture of 0.05 mols of tricarballylic acid, 0.15 mol of triethylamine and 150 ml of acetone in a flask was dropwise added 0.15 mols of methyl 2-(bromomethyl) acrylate at room temperature over a period of one hour, followed by stirring for 2 hours. To the mixture was added 300 ml of water, followed by stirring to deposit crystals. The crystals were collected by filtration and dried to obtain Compound F-24 in a yield of 90%. The melting point thereof was 63.0° C. The structure of the compound was confirmed by NMR, MASS and IR.

SYNTHESIS EXAMPLE 9

Synthesis of Compound F-25

A mixture of 0.05 mols of trimethylolethane, 0.15 mols of succinic anhydride, 0.30 mols of triethylamine and 150 ml of acetone was stirred in a flask at room temperature for 8 hours, and then 0.15 mols of methyl 2-(bromomethyl) acrylate was dropwise added thereto over a period of one hour, followed by stirring for 2 hours. To the mixture was added 300 ml of water, followed by stirring, and the mixture was extracted with ethyl acetate. The extract was dried on magnesium sulfate and filtered. The filtrate was sufficiently concentrated under a reduced pressure, separated by silica gel chromatography (hexane/ethyl acetate=8/2) and concentrated under a reduced pressure to obtain Compound F-25 in a yield of 60%. The melting point thereof was 38.0° C. The structure of the compound was confirmed by NMR, MASS and IR.

SYNTHESIS EXAMPLE 10

Synthesis of Compound F-27

A mixture of 0.1 mol of 1,2,3-tris(2-cyanoethoxypropane) and 100 ml of concentrated hydrochloric acid was refluxed by heating for 2 hours in a flask to deposit crystals (ammonium chloride). The concentrated hydrochloric acid was concentrated and acetone was added thereto, -followed by filtration to remove the deposited crystals. To the filtrate was added 1.0 mol of triethylamine, and then 0.3 mols of methyl 2-(bromomethyl)acrylate was dropwise added thereto over a period of one hour, followed by stirring for 2 hours. To the mixture was added 300 ml of water, followed by stirring, and the mixture was extracted with ethyl acetate. The extract was dried on magnesium sulfate and filtered. The filtrate was sufficiently concentrated under a reduced pressure, separated by silica gel chromatography (hexane/ ethyl acetate=7/3) and concentrated under a reduced pressure to obtain Compound F-27 as a semi-solid at room temperature in a yield of 20%. The structure of the compound was confirmed by NMR, MASS and IR.

The $^1$H NMR data (300 MHz, CDCl$_3$ solvent) of Compounds A-1, D-7 and F-25 are shown below for reference.
Compound A-1
δ 3.87(s, 3H, CH$_3$), 5.28(m, 1H, CH$_2$=CH—), 5.35(m, 2H, =CH—CH$_2$—), 6.31(m, 1H, CH$_2$=CH—), 7.11(m, 1H, ArH), 7.35(m, 2H, ArH), 7.52(m, 1H, ArH).
Compound D-7
δ 1.68(m, 4H, —CH$_2$—), 2.38(m, 4H, —CH$_2$CO$_2$—), 3.78 (s, 6H, CH$_3$), 4.80(m, 4H, =CH—CH$_2$—), 5.84(m, 2H, CH$_2$=CH—), 6.37(m, 2H, CH$_2$=CH—).
Compound F-25
δ 1.00(S, 3H, CH$_3$), 2.65(m, 12H, —CH$_2$CO$_2$—), 3.77(s, 9H, CH$_3$), 4.02(s, 6H, —CH$_2$OCO—), 4.82(m, 6H, =CH—CH$_2$—), 5.85(m, 3H, CH$_2$=CH—), 6.38(m, 3H, CH$_2$=CH—).

All specific compounds described above are synthesized in a similar manner as described above.

As described above, the radical polymerizable compound according to the present invention has at least one structure represented by formula (I), (II) or (III), and owing to the effect of substituent in the α-position thereof it is suitable for a radical polymerizable compound used in a photo-radical polymerization composition that is promising in image forming techniques.

By using the radical polymerizable compound according to the present invention, a photopolymerizable composition that is particularly suitable for a lithographic printing plate precursor capable of performing direct plate-making based on digital data, for example, from a computer by recording using a solid laser or semiconductor laser radiating an ultraviolet ray, visible light or infrared ray and that satisfies both high sensitivity and excellent preservation stability is provided.

While the invention has been described in detail and with reference to specific examples thereof, it will be apparent to one skilled in the art that various changes and modifications can be made therein without departing from the spirit and scope thereof.

What is claimed is:

1. A radical polymerizable compound comprising a structure represented by the following formula (I), (II) or (III):

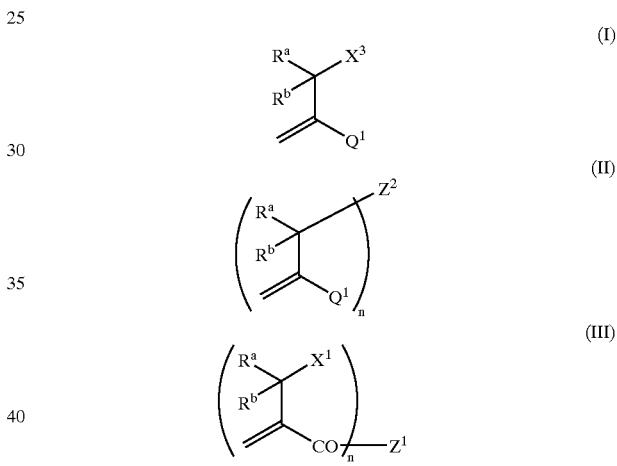

wherein $X^3$ represents a heterocyclic group that is connected through a hetero atom included therein; $Q^1$ represents a group represented by CN or COX$^2$; $X^2$ represents a hydroxy group, a substituted oxy group, a substituted thio group, an amino group, a substituted amino group, a heterocyclic group that is connected through a hetero atom included therein or a halogen atom; $X^1$ represents a substituted oxy group, a substituted amino group, a heterocyclic group that is connected through a hetero atom included therein or a halogen atom; $Z^1$ and $Z^2$ each represents a n-valent connecting group having at least 6 carbon atoms, in which the n's connecting parts are all hetero atoms; $R^a$ and $R^b$, which may be the same or different, each represents a hydrogen atom, a halogen atom, a cyano group or an organic residue; or $R^a$ and $R^b$, $X^1$ and $R^a$ or $R^b$, $X^3$ and $R^a$ or $R^b$, or $Q^1$ and $R^a$ or $R^b$ may combine with each other to form a cyclic structure; and n represents an integer of from 2 to 6.

2. The radical polymerizable compound as claimed in claim 1, wherein the compound is a compound represented by formula (I).

3. The radical polymerizable compound as claimed in claim 1, wherein the compound is a compound represented by formula (II).

4. The radical polymerizable compound as claimed in claim 1, wherein the compound is a compound represented by formula (III).

5. The radical polymerizable compound as claimed in claim 1, wherein $R^a$ and $R^b$, which may be the same or different, each represents a hydrogen atom, a halogen atom, a cyano group, a hydrocarbon group which may have a substituent and/or an unsaturated bond, a substituted oxy group, a substituted thio group, a substituted amino group, a substituted carbonyl group or a carboxylato group.

6. The radical polymerizable compound as claimed in claim 1, wherein in groups $X^1$, $X^2$ and $X^3$, the hetero atom is a non-metallic atom.

7. The radical polymerizable compound as claimed in claim 1, wherein in groups $X^1$, $X^2$ and $X^3$, the hetero atom is selected from the group consisting of an oxygen atom, a sulfur atom, a nitrogen atom and a phosphorus atom.

* * * * *